United States Patent [19]
Hakuta et al.

[11] Patent Number: 5,149,659
[45] Date of Patent: Sep. 22, 1992

[54] METHOD AND APPARATUS FOR ANALYZING FLUORINE CONTAINING GASES

[75] Inventors: Kohzo Hakuta, Fuchu; Minoru Aramaki, Tokyo; Takashi Suen. A, Yamaguchi; Mitsuo Kodama, Ube; Hisaji Nakano, Ube; Shinsuke Nakagawa, Ube, all of Japan

[73] Assignee: Central Glass Company, Limited, Ube, Japan

[21] Appl. No.: 666,691

[22] Filed: Mar. 5, 1991

Related U.S. Application Data

[62] Division of Ser. No. 330,898, Mar. 31, 1989, Pat. No. 5,017,499.

[30] Foreign Application Priority Data

Mar. 31, 1988 [JP] Japan ................................. 63-79088
Dec. 16, 1988 [JP] Japan ................................. 63-317658
Dec. 27, 1988 [JP] Japan ................................. 63-330115

[51] Int. Cl.$^5$ ........................ G01N 31/00; H01S 3/22
[52] U.S. Cl. ....................................... 436/55; 422/88; 422/93; 422/111; 372/59
[58] Field of Search .............. 436/101, 124, 136, 133, 436/55; 423/241, 178, 191, 179; 372/59; 422/88, 89, 90, 93, 83, 111

[56] References Cited

U.S. PATENT DOCUMENTS

| | | | |
|---|---|---|---|
| 2,925,327 | 2/1960 | Katz et al. | 436/124 |
| 3,579,305 | 5/1971 | Neti | 436/124 |
| 3,847,552 | 11/1974 | Hobgood et al. | 423/241 |
| 3,915,645 | 10/1975 | Funke et al. | 422/93 |
| 4,147,513 | 4/1979 | Bienkowski et al. | 436/145 |
| 4,298,347 | 11/1981 | Walsh | 436/133 |
| 4,637,987 | 1/1987 | Minten et al. | 436/167 |
| 4,740,982 | 4/1988 | Hakuta et al. | 372/59 |
| 5,017,499 | 5/1991 | Hakuta et al. | 436/124 |

FOREIGN PATENT DOCUMENTS 152519 12/1985 Japan.
101231 5/1986 Japan.

OTHER PUBLICATIONS

"The Merck Index" 10th ed., 596, New Jersey, Merck and Co., Inc., 1983.
"Inorganic and Theoretical Chemistry" vol. 3, J. W. Mellor, New York, Longmans, Green and Co., 1946.
Kaye, S. et al., "Electroanalytical Determination of Molecular Fluorine" Analytical Chemistry, vol. 40, No. 14, 2217-2218, 1968.
Macdonald, A. M. G. et al., "Fluorine" Encyclopedia of Industrial Chemical Analysis, vol. 13, 3-5, New York, London-Sydney-Toronto, 1971.

*Primary Examiner*—Robert J. Warden
*Assistant Examiner*—Jeffrey R. Snay
*Attorney, Agent, or Firm*—Fleit, Jacobson, Cohn, Price, Holman & Stern

[57] ABSTRACT

The concentration of molecular fluorine in a mixed gas such as an excimer laser gas can be determined easily, quickly and accurately by passing the mixed gas through a column packed with an alkali metal or alkaline earth metal compound which has no halogen atom and reacts with fluorine to form a solid fluoride together with molecular oxygen and/or carbon dioxide and measuring the concentration of oxygen or carbon dioxide in the fluorine-free gas flowed out of the packed column. If the mixed gas initially contains molecular oxygen or carbon dioxide, its concentration is measured separately after fixing fluorine in another column packed with an element which forms a fluoride. This analyzing method can be used in a feedback control system for controlling the concentration of fluorine in an excimer laser gas during operation of the laser to thereby stabilize the laser output power.

21 Claims, 3 Drawing Sheets

METHOD AND APPARATUS FOR ANALYZING FLUORINE CONTAINING GASES

This is a divisional of application Ser. No. 07/330,898, filed Mar. 31, 1989, now U.S. Pat. No. 5,017,499.

BACKGROUND OF THE INVENTION

This invention relates to the analysis of gases containing molecular fluorine, and more particularly to a method for determining at least the concentration of fluorine in a fluorine containing mixed gas and an apparatus for same. The method and apparatus according to the invention are particularly suitable for analyzing excimer laser gases containing fluorine.

Known methods for determining the concentration of fluorine in a mixed gas include wet methods and dry methods.

A typical example of the wet methods is an electroanalysis method using a LiCl solution cell in which chlorine ion is oxidized by absorption of fluorine gas. (Anal. Chem., 40, 2217 (1968).) In this method it is important to accomplish complete absorption of the sample gas in the LiCl solution, but in industrial applications it is troublesome to maintain optimum conditions of blowing the gas into the solution, and the analysis entails intricate instruments and operations.

An example of the dry methods has the steps of passing a fluorine containing gas through a column of NaCl to form chlorine gas, forcing the chlorine gas to be absorbed in NaOH solution and determining the hypochlorite formed in the solution by iodometric titration. (A.M.G. Macdonald et al, "Fluorine", Encyclopedia of Industrial Chemical Analysis, Vol. 13, New York-London-Sydney-Tronto, 1971.) Since this method uses two sequential reactions the instruments become complicated, and it is difficult to enhance accuracy. Also it is known to directly analyze a fluorine containing gas by gas chromatography with corrosion preventing measures such as use of nickel or an alternative special material for the parts contacting the sample gas and covering the thermal conductivity cell with PTFE. However, such measures raise the cost of the apparatus and reduce the sensitivity.

Meanwhile, some excimer lasers are using a fluorine containing gas such as a mixture of Ar, $F_2$ and He or Ne or a mixture of Kr, $F_2$ and He or Ne. In such a laser gas the content of $F_2$ is usually about 0.1-1 vol %. It is not seldom that during operation of an excimer laser of this category the laser output power gradually lowers mainly by reason of lowering of the concentration of fluorine in the laser gas and/or formation of impurity gases. Although impurity gases formed in an excimer laser gas can be removed periodically or continuously by an adsorption process or a cold-trap process, monitoring of fluorine concentration in the laser gas is presently almost impracticable because of intricateness of analyzing operations and difficulty of handling the sample gas.

SUMMARY OF THE INVENTION

It is an object of the present invention to provide a practicable method for accurately and quickly determining the concentration of fluorine in a mixed gas, preferably together with the concentration(s) of the other component(s), which method is useful to analyze an excimer laser gas containing fluorine during operation of the laser.

It is another object of the invention to provide an apparatus for analyzing a fluorine containing gas by a method according to the invention.

It is still another object of the invention to provide a method and apparatus for controlling the concentration of fluorine in an excimer laser gas by utilizing a gas analyzing method according to the invention to thereby stabilize the laser output power.

According to the invention there is provided a method of analyzing a mixed gas containing fluorine gas to determine at least the concentration of the fluorine gas, the method comprising the steps of (a) passing the mixed gas through a packed column comprising a compound which has no halogen atom and reacts with fluorine gas to form a solid fluoride and at least one of molecular oxygen and carbon dioxide, (b) measuring the concentration of predetermined one of molecular oxygen and carbon dioxide in a gas flowed from the packed column, and (c) converting the concentration of molecular oxygen or carbon dioxide measured at step (b) to the concentration of fluorine gas in the mixed gas.

The principal feature of the invention resides in that fluorine gas in the sample gas passed through the aforementioned packed column is "converted" (in a figurative sense) to another gaseous element or a gaseous compound having no fluorine atom while fluorine is fixed in the packed coloumn as a solid fluoride, so that the fluorine concentration in the sample gas is determined by measuring the concentration of that gaseous element or compound. Therefore, the difficulties and inconveniences in directly measuring the quantity of fluorine or a fluoride are completely eliminated.

Usually an alkali metal or alkaline earth metal hydroxide, oxide, carbonate, hydrogen carbonate, sulfate or nitrate is used in the packed column. For example, the reaction of fluorine with calcium hydroxide is represented by the equation (1).

$$F_2 + Ca(OH)_2 \rightarrow CaF_2 + H_2O + 1/2O_2 \qquad (1)$$

That is, 1 mol of $F_2$ is accurately "converted" to ½ mol of $O_2$. This relation holds also when a different salt of an alkali metal or alkaline earth metal is used. It is easy to accurately and quickly measure the concentration of oxygen in the gas flowed out of the packed column, and the fluorine concentration in the initial sample gas can be determined from the measured concentration of oxygen by very simple calculation. Conveniently the concentration of oxygen can be measured by a conventional oxygen sensor using stabilized zirconia.

When an alkali metal or alkaline earth metal carbonate or hydrogen carbonate is used in the packed column, the reaction is represented by the equation (2).

$$F_2 + CaCo_3 \rightarrow CaF_2 + CO_2 + \tfrac{1}{2}O_2 \qquad (2)$$

In this case (and also when a different carbonate or a hydrogen carbonate is used) 1 mol of $CO_2$ and ½ mol of $O_2$ are formed from 1 mol of $F_2$. Therefore, it is possible to determine the fluorine concentration in the initial sample gas by measuring the concentration of carbon dioxide in the gas flowed out of the packed column. For example, the concentration of carbon dioxide is measured by gas chromatography or infrared absorption spectrum analysis.

If the fluorine containing sample gas contains or may possibly contain $O_2$ or $CO_2$ to be measured after passing the gas through the aforementioned packed column, there is the need of determining the initial concentration of $O_2$ or $CO_2$ in the mixed gas. In such a case the method of the invention further comprises the steps of (d) passing the mixed gas through another packed column comprising an element which reacts with fluorine gas to form a fluoride, and (e) measuring the concentration of oxygen or carbon dioxide in the gas flowed out of said another packed column, and the aforementioned step (c) comprises the sub-step of comparing the concentration measured at step (b) with the concentration measured at step (e).

The purpose of the step (d) is preventing contact of fluorine with the device to measure the concentration of oxygen or carbon dioxide. Therefore, it is suitable to use an element, e.g. Fe, which reacts with fluorine to form a solid fluoride to thereby fix fluorine within the column of Fe or an alternative element. However, it is also possible to use an element, e.g. Si, which reacts with fluorine to form a gaseous fluoride. In that case, the gas containing the gaseous fluoride is passed through a supplementary column packed with an alkali metal or alkaline earth metal compound which reacts with the gaseous fluoride to form a solid fluoride, as represented by the equation (3).

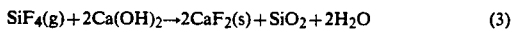

$$SiF_4(g)+2Ca(OH)_2 \rightarrow 2CaF_2(s)+SiO_2+2H_2O \quad (3)$$

In another aspect the invention provides an apparatus for analyzing a mixed gas containing fluorine gas to determine at least the concentration of the fluorine gas, the apparatus comprising a column packed with a compound which has no halogen atom and reacts with fluorine gas to form a solid fluoride and at least one of molecular oxygen and carbon dioxide, means for passing the mixed gas through the packed column, and a gas detecting means for measuring the concentration of predetermined one of molecular oxygen and carbon dioxide in a gas flowed out of the packed column.

Optionally the apparatus may further comprise another column packed with an element which reacts with fluorine gas to form a fluoride, and when that fluoride is a gaseous fluoride the apparatus further comprises a supplementary column which is connected to said another column and is packed with an alkali metal or alkaline earth metal compound which reacts with the gaseous fluoride to form a solid fluoride.

By using the present invention the concentration of fluorine in various kinds of mixed gases can be determined quickly and accurately by simple apparatus and operations. It is possible to determine even fluorine concentrations of the order of ppm. Besides fluorine concentration, the concentration of any other component of the mixed gas can easily be measured by a suitable analyzer because in most cases the "conversion" of fluorine to oxygen or carbon dioxide is accomplished without affecting the other component(s) of the mixed gas. The method and apparatus according to the invention are suitable for application to excimer lasers using a fluorine containing laser gas because changes in the concentration of fluorine in the laser gas can easily be detected while operating the laser and also because the concentration of rare gases too can be measured by using a suitable detection means.

Furthermore, the invention provides a method and a system for controlling the concentration of fluorine in an excimer laser gas during operation of the laser to thereby stabilize the laser output power. The control method comprises the steps of determining the concentration of fluorine in the excimer laser gas by analyzing sampled laser gas by the above stated method comprising the steps (a), (b) and (c), producing an electrical signal representing the determined concentration of fluorine in the laser gas, making a computing operation using said electrical signal to find a deviation of the concentration of fluorine in the laser gas from a predetermined concentration and producing a control signal representing an appropriate amount of supply of fluorine to the laser gas in the laser for cancellation of said deviation, and regulating the supply of fluorine to the laser gas in the laser based on the control signal. The control system comprises means for performing the respective steps of the control method.

Thus, the fluorine concentration in an excimer laser gas can accurately be detected during operation of the laser, and by feedback of the detected fluorine concentration to the fluorine supplying system the fluorine concentration is automatically regulated to the aimed concentration. Therefore, the excimer laser can continuously be operated for long hours with very stable output power.

DESCRIPTION OF THE PREFERRED EMBODIMENTS

Figure 1:
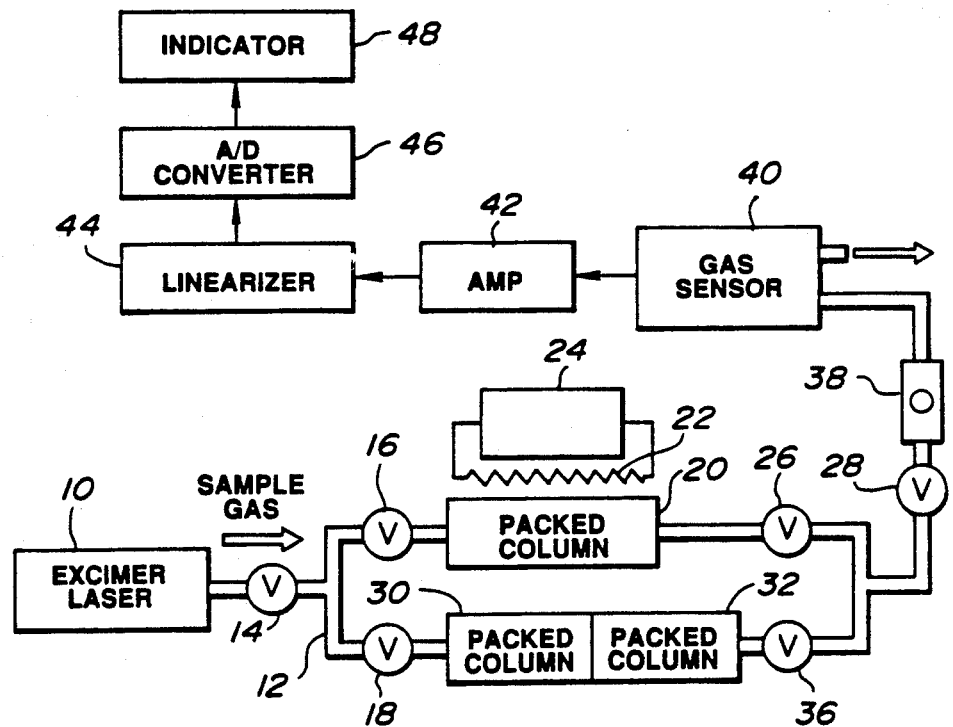
FIG. 1 is a diagrammatic illustration of an apparatus according to the invention for determining the concentration of fluorine in an excimer laser gas.

As an embodiment of the invention, FIG. 1 shows an apparatus for the determination of the concentration of fluorine in a gas mixture by measuring the amount of oxygen gas formed by reaction of fluorine with a selected reactant. Numeral 10 indicates a source of a mixed gas containing fluorine. For example, the gas source 10 is an excimer laser. The mixed gas will be referred to as sample gas. By piping 12 the gas source 10 is connected to first and second packed columns 20 and 30 which are arranged in parallel. The piping includes valves 14, 16 and 18 to introduce the sample gas into either the first packed column 20 or the second packed column 30.

The packing of the first column 20 contains at least one kind of alkali metal compound or alkaline earth metal compound which reacts with molecular fluorine to form oxygen gas and a metal fluoride. It is suitable to use a hydroxide such as lithium hydroxie, sodium hydroxide, potassium hydroxide, calcium hydroxide magnesium hydroxide, strontium hydroxide or barium hydroxide, an oxide such as lithium oxide, sodium oxide, potassium oxide, calcium oxide, magnesium oxide or barium oxide, or a carbonate such as lithium carbonate, sodium carbonate, potassium carbonate, magnesium carbonate, calcium carbonate, strontium carbonate or barium carbonate. Also it is possible to use hydrogen carbonate, sulfate or nitrate of an alkali metal or an alkaline earth metal. It is preferred to use soda lime which is essentially a mixture of calcium hydroxide, calcium oxide and sodium hydroxide, because soda lime readily reacts with fluorine to generate oxygen gas in a quantity accurately proportional to the quantity of fluorine gas brought into contact therewith. In any case it is favorable to use a fine powder of the selected compound or mixture.

It is possible to use the packed column 20 at room temperature, but it is preferable to keep this column heated at temperatures above 100° C. for efficient reaction of the packing with fluorine. The packed column 20 in FIG. 1 is provided with a heater 22 and a temperature control unit 24.

The structural material of the column 20 is not limited insofar as it is resistant to fluorine gas. For practical use the column 20 will be made of stainless steel or Monel metal, and in advance of actual use the column surface will be passivated by passing fluorine gas through the empty column. Usually the column 20 is about 10 mm in diameter and about 100 mm in length. A suitable quantity of the packing of the column 20 depends on the level of fluorine concentration in the gas to be analyzed. For practical purposes it is desirable that the gas analysis can be made 2000 times or more without replacing the packing. For example, for the purpose of measuring the concentration of fluorine in an excimer laser gas it suffices to pack the column 20 with about 10 g of soda lime.

The piping including valves 26 and 28 connects the outlet of the first packed column 20 to an oxygen sensor 40 via a flowmeter 28.

The oxygen sensor 40 is the detector in this gas analyzing apparatus. It is suitable to use an oxygen sensor of the concentration cell type having an oxygen ion conductive solid electrolyte layer. A gas subject to measurement is brought into cotact with one side of the electrolyte layer while the opposite side is exposed to a reference gas in which the concentration of oxygen is known. As the oxygen ion conductive electrolyte it is preferred to employ a stabilized zirconia, which is a sintered ceramic obtained by introducing a stabilizing oxide such as calcia or yttria into zirconia to form a solid solution. By operating the zirconia oxygen sensor at sufficiently high temperatures it is possible to accurately measure the concentration of oxygen in an unknown sample gas in less than one minute. It is suitable to keep the zirconia oxygen sensor 40 heated at a temperature above 500° C., and the atmospheric air can be used as the reference gas. The zirconia oxygen sensor is wide in dynamic range and can be used even for measurement of very low oxygen concentrations of the order of ppm since the output voltage of this sensor is proportional to the logarithm of the partial pressure of oxygen in the gas subject to measurement.

The second column 30 is packed with an element which reacts with fluorine gas to form a fluoride. That is, the packing can be selected from various elements such as, for example, Fe, Cr, Mn, Co, Zn, Ti, Zr, Sn and Pb each of which forms a solid fluoride, (represented by $FeF_3$) by direct reaction with fluorine, and Si, Ge, P, Sb, S, Se, Te, W, Mo and V each of which forms a gaseous fluoride (represented by $SiF_4$) by direct reaction with fluorine. In any case it is favorable to use a fine powder of the selected element.

The purpose of the second packed column 30 is removing fluorine from the sample gas without varying the concentration of oxygen in the gas. When the column 30 is packed with an element which forms a solid fluoride, fluorine contained in the sample gas is fixed within this column 30. In that case the column 32 shown in FIG. 1 is unnecessary, and the outlet of the second packed column 30 is connected to the oxygen sensor 40 via valves 36 and 28 and the flowmeter 28. When the column 30 is packed with an element which forms gaseous fluoride, the apparatus includes a third packed column 32 subsequent to and in series with the second column 30. The third column 32 is packed with a compound which reacts with the gaseous fluoride formed in the second column 30 to form a solid fluoride. As the packing of the third column 32 it is suitable to use an alkali metal compound or an alkaline earth metal compound, which may be hydroxide, oxide, carbonate, hydrogen carbonate, sulfate or nitrate. That is, the packing of the third column 32 is analogous to that of the first column 20. The purpose of fixing fluorine in the second or third packed column 30, 32 is for preventing the oxygen sensor 40 from being damaged by fluorine.

It is possible to use the second and third columns 30 and 32 at room temperature, but it is preferable to keep these columns 30, 32 at temperatures above 100° C. by using heater (not shown). The structural material and dimensions of the second and third columns 30, 32 are as described above with respect to the first column 20.

For treatment of the output voltage of the oxygen sensor 40 the gas analyzing apparatus includes amplifier 42, linearizer 44 and A/D converter 46. Using the treated signal, an indicator 48 indicates the concentration of oxygen in the gas passed to the oxygen sensor 40.

Using the apparatus of FIG. 1, the concentration of fluorine in the sample gas is determined in the following way.

First the valves 14, 16, 26 and 28 are opened to pass the sample gas through the first packed column 20 at a constant flow rate for a suitable length of time, which ranges from tens of seconds to several minutes. Then the output of the oxygen sensor 40 represents an oxygen concentration $P_1$, which is the sum of the concentration of oxygen derived from fluorine contained in the sample gas and the concentration of oxygen initially contained in the sample gas.

Next, the valves 14, 18, 36 and 28 are opened (closing the valves 16 and 26) to pass the sample gas through the second and third packed columns 30 and 32 at the aforementioned constant flow rate. Then the output of the oxygen sensor 40 represents an oxygen concentration $P_2$, which is the concentration of oxygen initially contained in the sample gas. That is, $P_1 - P_2$ is an oxygen concentration indicative of the concentration of fluorine in the sample gas.

From the oxygen concentrations $P_1$ and $P_2$ indicated by the indicator 48 the concentration of fluorine in the sample gas can instantly be found by precedently calibrating the oxygen sensor 40 with either a fluorine gas of a known concentration or an oxygen gas of a known concentration. Since 1 mol of $F_2$ gas is converted into $\frac{1}{2}$ mol of $O_2$ gas in the first column 20 as explained hereinbefore with reference to equation (1), the concentration of fluorine in the sample gas is found by calculating $2K(P_1 - P_2)$, where K is a correction factor.

If it is known that the sample gas does not contain oxygen gas, it is unnecessary to measure the aforementioned $P_2$ by using the second column 30 or the combination of the second and third columns 30, 32.

The determination of fluorine by the above described apparatus and method can be accomplished irrespective of the pressure of the sample gas insofar as the defluorinated gases are fed to the oxygen sensor 40 at a constant flow rate, which may range from about 10 cm$^3$/min to about 1000 cm$^3$/min.

REFERENTIAL EXAMPLE 1

In the apparatus of FIG. 1 the piping 12 was made of stainless steel (SUS 316), and the first column 20 was a Monel metal column 8 mm in inner diameter and 100 mm in length. In sections where fluorine containing gases flow the piping was passivated in advance by passing fluorine gas therethrough. The first column 20 was packed with 8 g of soda lime powder.

To confirm the performance of the first column 20, helium gas containing 0.5 vol % of fluorine gas was passed through the first column 20 under various conditions shown in Table 1, and the gas passed through the column 20 was introduced into a column (not shown) packed with potassium iodide powder. If the gas still contains fluorine the potassium iodide powder changes its color. By preliminary testing this method proved to be capable of detecting fluorine even when fluorine concentration is as low as 100 ppb.

TABLE 1

| Run No. | Temp. of Soda lime Column (°C.) | Gas Flow Rate (cm$^3$/min) | Velocity of Gas Flow (m/s) |
|---|---|---|---|
| 1 | 150 | 800 | 0.15 |
| 2 | 150 | 1200 | 0.22 |
| 3 | 150 | 1900 | 0.35 |
| 4 | 150 | 2500 | 0.46 |
| 5 | 150 | 3100 | 0.57 |
| 6 | 150 | 3900 | 0.72 |
| 7 | 200 | 800 | 0.15 |
| 8 | 200 | 1200 | 0.22 |
| 9 | 200 | 1900 | 0.35 |
| 10 | 200 | 2500 | 0.46 |
| 11 | 200 | 3100 | 0.57 |
| 12 | 200 | 3900 | 0.72 |

In every run the gas was continuously passed through the soda lime column and the potassium iodide column for 5 min, and in every run no change was observed in the color of the potassium iodide powder. Thus, it was evidenced that complete reaction of fluorine with soda lime takes place in the column 20 even when the flow rate of the gas passing through the column is far higher than usual flow rates (about 100 cm$^3$/min) in actual gas analyzing operations.

REFERENTIAL EXAMPLE 2

In the apparatus of FIG. 1, the second column 30 was a Monel metal column 10 mm in inner diameter and 100 mm in length. After passivation by fluorine gas, the second column 30 was packed with 5 g of Si powder. The third column 32 was identical with the first column (packed with soda lime) in Referential Example 1.

Using a helium gas containing 0.5 vol % of fluorine gas, the fluorine fixing performance of the second and third columns 30, 32 was tested by the same method as in Referential Example 1. The test conditions were as shown in Table 2.

In every run the gas was continuously passed through the Si powder column 30, soda lime column 32 and the potssium iodide column (not shown) for 5 min, and in every run the potassium iodide powder exhibited no change in color. Thus, it was evidenced that complete fixing of fluorine can be accomplished in the suitably heated second and third columns 30, 32 when the flow rate of the sample gas is as is usual, and even when the flow rate is considerably higher.

TABLE 2

| Run No. | Temp. of Packed Columns (°C.) | Gas Flow Rate (cm$^3$/min) | Velocity of Gas Flow (m/s) |
|---|---|---|---|
| 1 | 150 | 600 | 0.11 |
| 2 | 150 | 800 | 0.15 |
| 3 | 150 | 900 | 0.17 |
| 4 | 200 | 600 | 0.11 |
| 5 | 200 | 800 | 0.15 |
| 6 | 200 | 1200 | 0.22 |
| 7 | 200 | 1900 | 0.35 |
| 8 | 200 | 2500 | 0.46 |
| 9 | 200 | 3100 | 0.57 |
| 10 | 200 | 3900 | 0.72 |

EXAMPLE 1

Using the apparatus of FIG. 1 and a gas bomb in place of the excimer laser 10, a helium gas containing a known amount of fluorine gas was analyzed. The concentration of fluorine in the sample gas was carefully regulated to 0.1%, 0.2%, 0.3%, 0.4% or 0.5% by volume. The first column 20 was a Monel metal column 8 mm in diameter and 100 mm in length and was packed with 8 g of soda lime powder (identical with the column in Referential Example 1). The second and third columns 30 and 32 were not used since every sample gas was free of oxygen. The packed column 20 was kept heated at about 150° C. The oxygen sensor 40 was of the concentration cell type using stabilized zirconia. In every run the flow rate of the sample gas was 100 cm$^3$/min.

Figure 2:
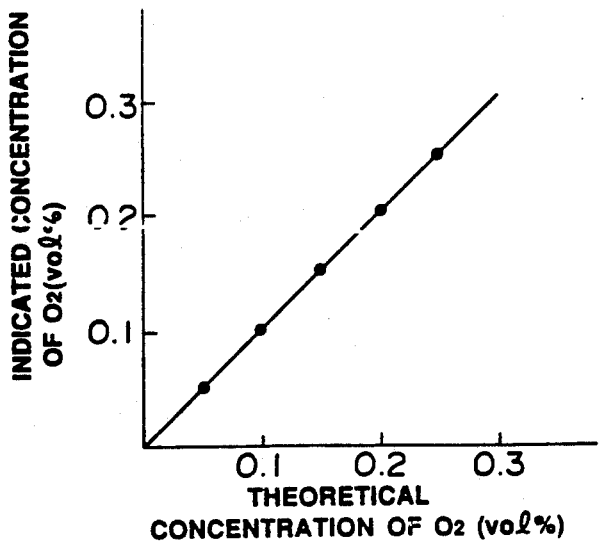
FIG. 2 is a graph showing the result of a test on the accuracy of an oxygen sensor used in the apparatus of FIG. 1.

The results were as shown in Table 3 and FIG. 2.

TABLE 3

| Run No. | Fluorine Concentration in Sample Gas (vol %) | Theoretical Concentration of Oxygen at Outlet of Soda Lime Column (vol %) | Oxygen Concentration indicated by Zirconia Oxygen Sensor (vol %) |
|---|---|---|---|
| 1 | 0.100 | 0.050 | 0.051 |
| 2 | 0.200 | 0.100 | 0.102 |
| 3 | 0.300 | 0.150 | 0.149 |
| 4 | 0.400 | 0.200 | 0.198 |
| 5 | 0.500 | 0.250 | 0.252 |

As can be seen in Table 3 and FIG. 2, the concentration values indicated by the zirconia oxygen sensor approximately agreed with the theoretical values, and there was a linear relationship between the indicated and theoretical values. That is, simple conversion of the indicated oxygen concentration into fluorine concentration could be taken as the actual concentration of fluorine in the sample gas.

EXAMPLE 2

The measurement operation of Example 1 was repeated except that the sample gases were further diluted by helium gas. In Run Nos. 1, 2 and 3 of this example, the concentrations of fluorine in the sample gases were 50 ppm, 100 ppm and 150 ppm, respectively, and the fluorine concentrations found by conversion of oxygen concentrations indicated by the zirconia oxygen sensor were 46 ppm, 110 ppm and 150 ppm, respectively. The measurements can be taken as fairly accurate considering the lowness of fluorine concentrations in the sample gases.

EXAMPLE 3

The measurement operation of Example 1 was modified in the following points.

About 0.05 vol % of oxygen was added to each sample gas. Besides the determination of fluorine by using the first packed column 20, measurement of the initial concentration of oxygen in each sample gas was made by using the second and third packed columns 30 and 32. The second column 30 was a passivated Monel metal column 10 mm in inner diameter and 100 mm in length and was packed with 5 g of Si powder. The third column 32 was identical with the first column 20 (packed with soda lime). The second and third columns 30, 32 were kept heated at about 150° C. The results are shown in Table 4.

TABLE 4

| | Sample Gas | | Measurement using 1st Column | | Measurement using 2nd & 3rd Columns | |
|---|---|---|---|---|---|---|
| | | | Theo-retical | Indi-cated | Theo-retical | Indi-cated |
| Run No. | Fluorine Concen-tration (vol %) | Oxygen Concen-tration (vol %) | Oxygen Concen-tration (vol %) | Oxygen Concen-tration (vol %) | Oxygen Concen-tration (vol %) | Oxygen Concen-tration (vol %) |
| 1 | 0.100 | 0.050 | 0.100 | 0.102 | 0.050 | 0.050 |
| 2 | 0.200 | 0.050 | 0.150 | 0.149 | 0.050 | 0.049 |
| 3 | 0.300 | 0.050 | 0.200 | 0.197 | 0.050 | 0.052 |
| 4 | 0.400 | 0.050 | 0.250 | 0.253 | 0.050 | 0.052 |
| 5 | 0.500 | 0.050 | 0.300 | 0.304 | 0.050 | 0.048 |

The above results demonstrate that even when the sample gas contains oxygen the determination of fluorine concentration can be accomplished without problem.

COMPARATIVE EXAMPLE 1

Figure 3:
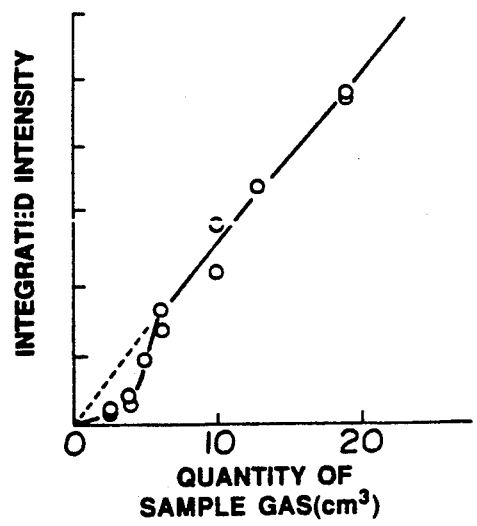
FIG. 3 is a graph showing the result of a trial of determining the concentration of fluorine in a known gas mixture by reacting fluorine with sodium chloride to form chlorine gas and measuring the chlorine gas by gas chromatography.

As a trial, the concentration of fluorine in a known sample gas was measured by passing the sample gas through a column packed with sodium chloride and measuring the quantity of chlorine gas formed by the reaction in the packed column with a corrosion resistant gas chromatography apparatus using HID. A nickel tube 10 mm in inner diameter and 200 mm in length was packed with NaCl and was interposed between a gas sampler and the gas chromatography apparatus. A variable quantity of a helium gas containing 0.5 vol % of fluorine was taken into the gas sampler, and a carrier gas was passed through the gas sampler, sodium chloride column and gas chromatography apparatus to measure integral intensity of the peak of chlorine. FIG. 3 shows the relationship between the volume of the fluorine containing helium gas taken into the gas sampler (converted to the volume under normal pressure) and the integral intensity by gas chromatography. Apparently this method is problematic as to accuracy and reproducibility when only a small quantity of fluorine is subjected to measurement.

Figure 4:
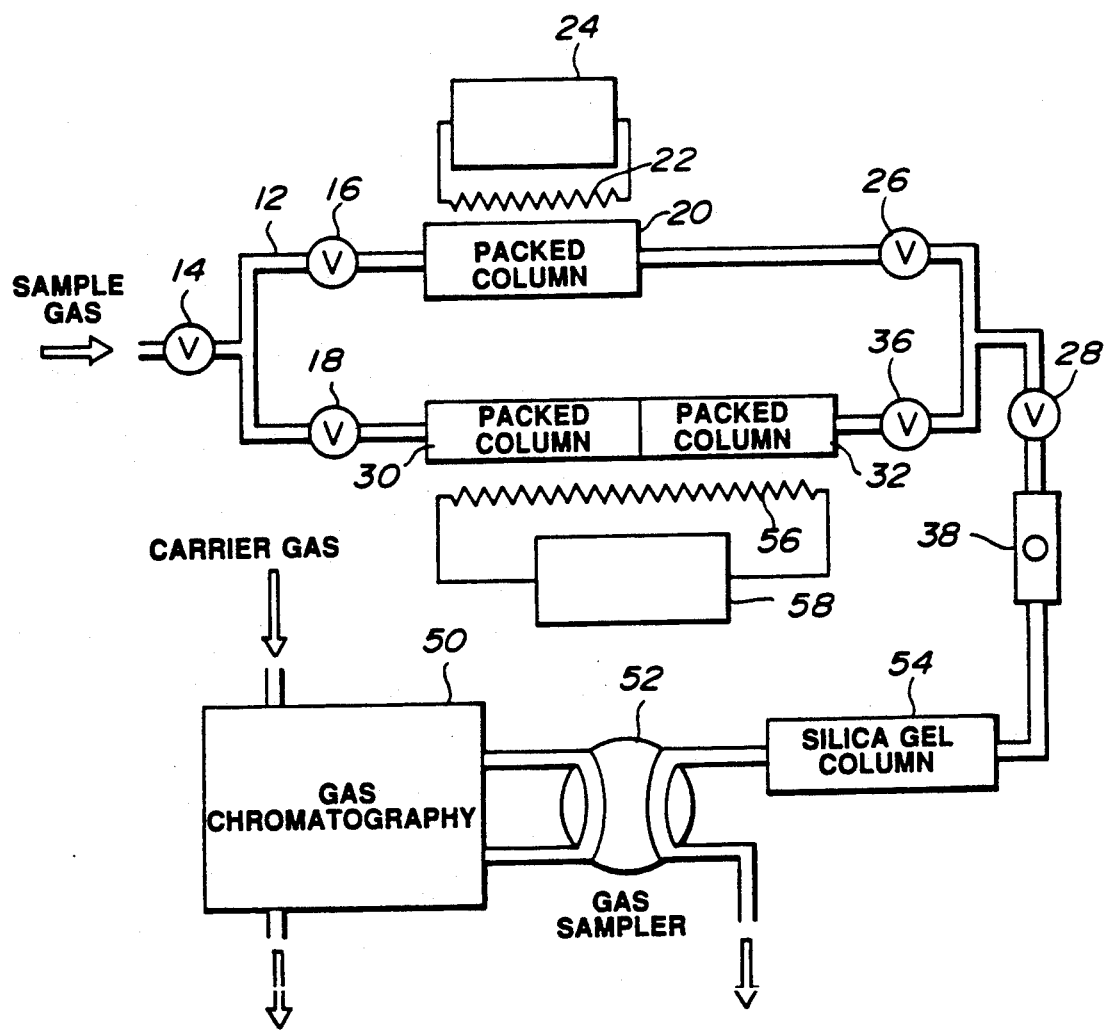
FIG. 4 is a diagrammatic illustration of another apparatus according to the invention for analyzing a mixed gas containing fluorine.

FIG. 4 shows a modification of the apparatus of FIG. 1 in respect of the means to measure the concentration of oxygen in the gas flowing out of the first packed column 20 or the third packed column 32 (or the second packed column 30 when the third column 32 is omitted). The apparatus of FIG. 4 employs a gas chromatography apparatus 50 in place of the oxygen sensor and the electrical signal treating components in FIG. 1. The gas chromatography apparatus 50 is provided with a gas sampler 52, and, as is usual, a silica gel column 54 is interposed between the flowmeter 38 and the gas sampler 52. Numeral 56 indicates an optional heater for the second and third columns 30, 32, and numeral 58 a temperature control unit.

According to the present invention the gases to be analyzed with the gas chromatography apparatus 50 do not contain fluorine which is detrimental to the detector. Therefore, there is no problem in using an ordinary gas chromatography apparatus unless the sample gas contains a corrosive gas other than fluorine. This invention is mainly concerned with gases containing fluorine as the sole corrosive gas.

A merit of employing gas chromatography is that not only fluorine but also other components of the sample gas can be determined quickly. Various kinds of gas mixtures can be analyzed by this method, and for almost every component of a fluorine containing sample gas accurate determination is possible over a wide range of concentration, from about 1 ppm to tens of percent. The concentrations of the sample gas components can instantly be found from the gas chromatogram by preliminarily measuring the retention time for each component and plotting a calibration curve showing the relationship between the peak area and the concentration.

This method is very favorable for analysis of an excimer laser gas because the concentration of the important rare gas(es) such as Kr, Xe, Ar and/or Ne can be measured together with the concentration of $F_2$. As the packing of the gas chromatography column for determining the important components of excimer laser gases it is suitable to employ a so-called porous polymer, which is formed of a copolymer of styrene and divinylbenzene. With the porous polymer packing the retention time is known for each component of excimer laser gases.

According to the need it is possible to jointly use an oxygen sensor and a gas chromatography apparatus in a gas analyzing apparatus embodying the invention.

EXAMPLE 4

In the apparatus of FIG. 4 the first column 20 was packed with soda lime powder as in Example 1. In the gas chromatography apparatus 50, the column was 3 mm in diameter and 3 m in length and was packed with a porous polymer, Porapak Q of Waters Co., which was a styrenedivinylbenzene copolymer. The column temperature was 30° C. The carrier gas was helium gas, and its flow rate was 50 cm³/min.

First, helium gas containing known amounts of oxygen gas and krypton gas was passed through the first packed column 20 for more than 30 sec at a constant rate of 50 cm³/min. The flowing gas was sampled by the sampler 52 and analyzed in the gas chromatography apparatus 50 to plot a calibration curve indicating the relationship between the peak area and concentration (vol %) for each of $O_2$ and Kr.

Then, specially prepared sample gases were analyzed under the same conditions. Each sample gas was a helium gas containing known amounts of $F_2$ and Kr as shown in Table 5. Since every sample gas introduced into the soda lime column 20 was free of oxygen the second and third columns 30, 32 in FIG. 4 were not used. The concentrations of $O_2$ and Kr in the gas taken into the gas chromatography apparatus were determined from the peak areas of the respective elements by using the calibration curves, and the concentration of $F_2$ was determined by doubling the determined concentration of $O_2$. The results were as shown in Table 5, which indicate that the tested method and apparatus are fully practicable.

TABLE 5

| | Sample Gas | | Analytical Values | | |
|---|---|---|---|---|---|
| | | | | | $F_2$ |
| Run No. | Kr (vol %) | $F_2$ (vol %) | Kr (vol %) | $O_2$ (vol %) | (by conversion) (vol %) |
| 1 | 5.00 | 0.100 | 4.95 | 0.049 | 0.098 |
| 2 | 5.00 | 0.200 | 4.88 | 0.102 | 0.204 |
| 3 | 5.00 | 0.300 | 5.04 | 0.151 | 0.302 |
| 4 | 5.00 | 0.400 | 4.96 | 0.198 | 0.396 |
| 5 | 3.00 | 0.100 | 2.88 | 0.052 | 0.104 |
| 6 | 3.00 | 0.200 | 3.05 | 0.098 | 0.196 |
| 7 | 3.00 | 0.300 | 3.00 | 0.151 | 0.302 |
| 8 | 3.00 | 0.400 | 2.97 | 0.196 | 0.392 |

EXAMPLE 5

In this example known mixtures of neon gas, argon gas and fluorine gas were employed as sample gases, and analysis was carried out by the same process as in Example 4 except the following modifications in the gas chromatography apparatus.

The packing of the column was a porous polymer, Gaskuropack 54 of Gasukuro Kogyo Co., which was a styrene-divinylbenzene copolymer. The column was 3 mm in diamter and 6 m in length and was maintained at −72° C. with a dry ice-acetone bath. The flow rate of the carrier gas (helium gas) was 30 cm³/min.

The compositions of the sample gases and the results of analysis are shown in Table 6.

EXAMPLE 6

A sample gas consisting of 5.00 vol % of Kr, 0.200 vol % of $F_2$, 0.050 vol % of $O_2$ and 94.75 vol % of He was analyzed with the apparatus of FIG. 4.

The first column 20 and the third column 32 were packed with soda lime powder, and the second column 30 was packed with silicon powder. These three columns 20, 30, 32 were kept heated at 150° C. The particulars of the gas chromatography apparatus 50 were the same as in Example 4.

When the sample gas was passed through the first packed column 20 without using the second and third columns 30 and 32, the gas chromatography indicated that the concentration of Kr was 5.05 vol % and the concentration of $O_2$ was 0.143 vol %. When the sample gas was passed through the second and third packed columns 30 and 32 without using the first column 20, the gas chromatography indicated that the concentration of Kr was 4.96 vol % and the concentration of $O_2$ was 0.047 vol %. Consequently the composition of the sample gas was determined to be 5.01 vol % of Kr, 0.192 vol % {2×(0.143−0.047) vol %} of $F_2$, 0.047 vol % of $O_2$ and 94.75 vol % of He.

The apparatus of FIG. 4 is of use also in the case of converting fluorine in the sample gas to carbon dioxide by reaction in the first packed column 20. In that case the first column 20 is packed with carbonate or hydrogen carbonate of an alkali metal or an alkaline earth metal, such as sodium (hydrogen) carbonate, potassium (hydrogen) carbonate, lithium (hydrogen) carbonate, calcium (hydrogen) carbonate, barium (hydrogen) carbonate or magnesium (hydrogen) carbonate. It is desirable to use a fine powder of a selected carbonate or hydrogen carbonate, and it is preferable to use the packed column 20 at temperatures above 100° C. As explained hereinbefore, the reaction of 1 mol of $F_2$ with an alkali metal or alkaline earth metal carbonate or hydrogen carbonate forms 1 mol of $CO_2$.

When the fluorine containing sample gas is an excimer laser gas, a porous polymer formed of a styrene-divinylbenzene copolymer is suitable as the packing of the gas chromatography column for measuring the concentrations of carbon dioxide and rare gases in the gas flowing out of the first packed column 20.

The second packed column 30 is used, either singly or together with the third packed column 32, in measuring the concentration of carbon dioxide initially contained in the fluorine containing sample gas. That is, the packing of the second column 30 is a substance which can convert fluorine gas in the sample gas into a fluoride without varying the concentration of carbon dioxide in the sample gas. Therefore, the second packed column

TABLE 6

| | Sample Gas | | | Analytical Values | | | |
|---|---|---|---|---|---|---|---|
| | | | | | $F_2$ (by con- | | |
| Run No. | $F_2$ (vol %) | Ar (vol %) | Ne (vol %) | $O_2$ (vol %) | version) (vol %) | Ar (vol %) | Ne (vol %) |
| 1 | 0.100 | 5.00 | 94.9 | 0.046 | 0.092 | 4.94 | 95.0 |
| 2 | 0.200 | 5.00 | 94.8 | 0.097 | 0.194 | 4.89 | 94.9 |
| 3 | 0.300 | 5.00 | 94.7 | 0.153 | 0.306 | 4.86 | 94.8 |
| 4 | 0.400 | 5.00 | 94.6 | 0.204 | 0.408 | 4.96 | 94.6 |
| 5 | 0.100 | 3.00 | 96.9 | 0.048 | 0.096 | 3.05 | 97.0 |
| 6 | 0.200 | 3.00 | 96.8 | 0.098 | 0.196 | 3.03 | 96.8 |
| 7 | 0.300 | 3.00 | 96.7 | 0.148 | 0.296 | 3.08 | 96.6 |
| 8 | 0.400 | 3.00 | 96.6 | 0.204 | 0.408 | 2.97 | 96.6 |

30 and the third packed column 32 may be identical with the counterparts in the case of converting fluorine to oxygen in the first packed column 20. For example, the second column 30 is packed with Fe powder to fix fluorine as solid $FeF_3$ to thereby omit the third column 32, or the second column 30 is packed with Si and the third column with calcium hydroxide powder to convert $SiF_4$ gas formed in the second column into solid $CaF_2$. It is also possible to pack the second column 30 with an alkali metal or alkaline earth metal compound such as hydroxide, oxide, sulfate or nitrate, or a suitable mixture such as soda lime, which reacts with fluorine to form a metal fluoride. In this case the third column 32 is unnecessary.

When the fluorine containing sample gas is passed through the first packed column 20, the concentration of $CO_2$ in the gas taken into the gas chromatography apparatus 50 will be determined to be $P_1$. When the same sample gas is passed through the second (and third) packed column(s) 30 (and 32) the initial concentration of $CO_2$ in the sample gas will be determined to be $P_2$. Then the concentration of $F_2$ in the sample gas is given by $K(P_1-P_2)$, where K is a correction factor, since 1 mol of $F_2$ is converted to 1 mol of $CO_2$ in the first packed column 20.

Alternative to the gas chromatography apparatus 50, an infrared absorption spectrum analyzer (will be referred to as IR analyzer) can be used. In that case, an infrared analyzer including an IR cell is provided subsequent to the silica gel column 54 in FIG. 4, or an IR cell alone is provided there and after complete replacement of the interior of the cell by the gas containing carbon dioxide is detached from the illustrated apparatus and attached to an IR analyzer.

In the case of using an IR analyzer, the concentrations of fluorine in the sample gas can be determined by preliminarily plotting a curve showing the relationship between carbon dioxide concentration and infrared absorption intensity. With an IR analyzer it is difficult to determine the concentration of every component of the sample gas, and it is necessary that the sample gas components other than carbon dioxide do not greatly vary. When the gas to be analyzed is high in the concentration of carbon dioxide the gas needs to be diluted at a known dilution ratio, because a nearly linear relationship between concentration and IR absorption intensity holds only when the concentration is below several percent.

As a still different way, the first column 20 in FIG. 4 may be packed with an element which reacts with fluorine gas to form a gaseous fluoride. For example, such an element can be selected from Si, Ge, P, Sb, Se, Te, W, Mo, V and B. In the case of Si or Ge, 2 mols of $F_2$ is converted into 1 mol of a fluoride gas. In the case of B, 3 mols of $F_2$ is converted into 2 mols of boron fluoride gas. In the case of P, Sb or V, 5 mols of $F_2$ is converted into 2 mols of a fluoride gas. In the case of Se, Te, W or Mo, 3 mols of $F_2$ is converted into 1 mol of a fluoride gas. By measuring the concentration of the fluoride gas in the gas flowed out of the packed column 20 by either gas chromatography or IR absorption spectrum analysis, the concentration of fluorine in the sample gas can be determined. In this case the second and third columns 30, 32 are unnecessary unless the sample gas contains a fluoride gas besides molecular fluorine. However, this method is rather inconvenient because fluoride gases are generally corrosive and toxic.

EXAMPLE 7

In the apparatus of FIG. 4 the first column 20 was a Monel metal column 8 mm in diameter and 100 mm in length, which was packed with 10 g of sodium carbonate powder. The second and third columns 30, 32 were not used.

In the gas chromatography apparatus 50 the packing of the column was Porapak Q, a porous polymer mentioned hereinbefore. The column was 2.3 mm in diameter and 1 m in length and was maintained at 30° C. The carrier gas was helium gas, and its flow rate was 25 $cm^3$/min. Under these conditions the retention time was 0.24 min for $O_2$ and 0.65 min for $CO_2$.

Preliminarily, helium gas containing variable and known amounts of $F_2$ and Kr were passed through the first packed column 20 for more than 30 sec at a rate of 50 $cm^3$/min, and the gas flowed out of the packed column 20 was taken into the gas chromatography apparatus 50 by the gas sampler 52 to plot a calibration curve, for each of $CO_2$ and Kr, showing the relation between the concentration of the gas component and the peak area.

Then, specially prepared sample gases were analyzed under the same conditions. Each sample gas was a helium gas containing known amounts of $F_2$ and Kr as shown in Table 7. The concentrations of the components of the gas taken into the gas chromatography apparatus were determined from the peak areas of the respective components by using the calibration curves, and the determined concentration of $CO_2$ was taken as the concentration of $F_2$ in the sample gas introduced into the first packed column 20.

The results were as shown in Table 7, which indicate that the tested method and apparatus are fully practicable.

TABLE 7

| | Sample Gas | | Analytical Values | | |
|---|---|---|---|---|---|
| | | | | | $F_2$ |
| Run No. | Kr (vol %) | $F_2$ (vol %) | Kr (vol %) | $CO_2$ (vol %) | (by conversion) (vol %) |
| 1 | 5.00 | 0.100 | 4.95 | 0.093 | 0.093 |
| 2 | 5.00 | 0.200 | 4.88 | 0.205 | 0.205 |
| 3 | 5.00 | 0.300 | 5.04 | 0.300 | 0.300 |
| 4 | 5.00 | 0.400 | 4.96 | 0.393 | 0.393 |
| 5 | 3.00 | 0.100 | 2.88 | 0.091 | 0.091 |
| 6 | 3.00 | 0.200 | 3.05 | 0.185 | 0.185 |
| 7 | 3.00 | 0.300 | 3.00 | 0.296 | 0.296 |
| 8 | 3.00 | 0.400 | 2.97 | 0.384 | 0.384 |

EXAMPLE 8

In this example known mixtures of neon gas, argon gas and fluorine gas were employed as sample gases, and analysis was carried out by the same process as in Example 7 except the following modifications in the gas chromatography apparatus.

The packing of the column was Gaskuropack 54, a porous polymer mentioned hereinbefore. The column was 3 mm in diamter and 6 m in length and was maintained at −72° C. with a dry ice-acetone bath. The flow rate of the carrier gas (helium gas) was 30 $cm^3$/min.

The compositions of the sample gases and the results of analysis are shown in Table 8.

TABLE 8

| Run No. | Sample Gas | | | Analytical Values | | | |
|---|---|---|---|---|---|---|---|
| | $F_2$ (vol %) | Ar (vol %) | Ne (vol %) | $CO_2$ (vol %) | $F_2$ (by conversion) (vol %) | Ar (vol %) | Ne (vol %) |
| 1 | 0.100 | 5.00 | 94.9 | 0.108 | 0.108 | 4.94 | 95.0 |
| 2 | 0.200 | 5.00 | 94.8 | 0.211 | 0.211 | 4.89 | 94.9 |
| 3 | 0.300 | 5.00 | 94.7 | 0.295 | 0.295 | 4.86 | 94.8 |
| 4 | 0.400 | 5.00 | 94.6 | 0.404 | 0.404 | 4.96 | 94.6 |
| 5 | 0.100 | 3.00 | 96.9 | 0.097 | 0.097 | 3.05 | 96.9 |
| 6 | 0.200 | 3.00 | 96.8 | 0.204 | 0.204 | 3.03 | 96.8 |
| 7 | 0.300 | 3.00 | 96.7 | 0.302 | 0.302 | 3.08 | 96.6 |
| 8 | 0.400 | 3.00 | 96.6 | 0.403 | 0.403 | 2.97 | 96.6 |

EXAMPLE 9

A sample gas consisting of 5.00 vol % of Kr, 0.200 vol % of $F_2$, 0.050 vol % of $CO_2$ and 94.75 vol % of He was analyzed with the apparatus of FIG. 4.

The first column 20 was packed with sodium hydrogen carbonate powder. The second column 30 was packed with silicon powder and the third column 32 with soda lime powder. Each of these columns 20, 30, 32 was a stainless steel column 10 mm in diameter and 100 mm in length, which was passivated by fluorine gas. These three columns 20, 30, 32 were kept heated at 150° C. The particulars of the gas chromatography apparatus 50 were the same as in Example 7.

When the sample gas was passed through the first packed column 20 without using the second and third columns 30 and 32, the gas chromatography indicated that the concentration of Kr was 5.08 vol % and the concentration of $CO_2$ was 0.255 vol %. When the sample gas was passed through the second and third packed columns 30 and 32 without using the first column 20, the gas chromatography indicated that the concentration of Kr was 4.96 vol % and the concentration of $CO_2$ was 0.053 vol %. Consequently the composition of the sample gas was determined to be 5.08 vol % of Kr, 0.202 (0.255−0.053) vol % of $F_2$, 0.053 vol % of $CO_2$ and 94.67 vol % of He.

Figure 5:
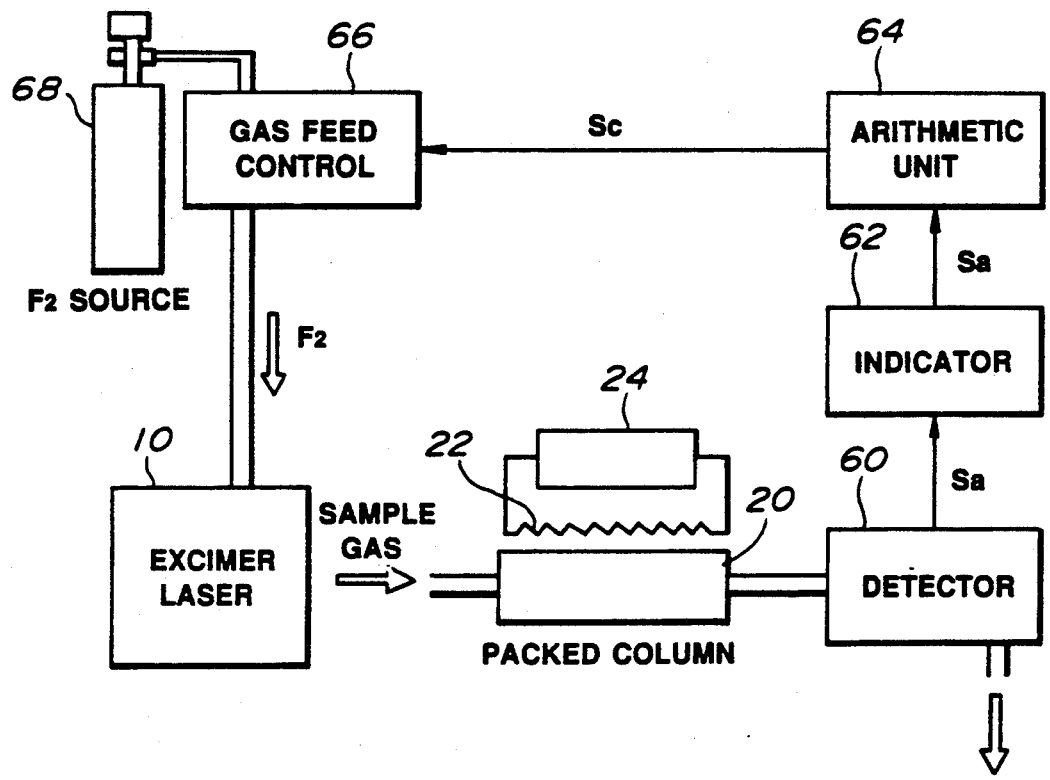
FIG. 5 is a diagrammatic illustration of an apparatus according to the invention for controlling the concentration of fluorine in a laser gas of an excimer laser.

FIG. 5 shows a control system according to the invention for stabilizing the output of an excimer laser 10 by controlling the concentration of fluorine in the laser gas. The control system includes a gas analyzing apparatus according to the invention.

In this control system the packed column 20 described with reference to FIGS. 1 and 4 is used to convert fluorine in the sample gas extracted from the excimer laser 10 to either oxygen or carbon dioxide. The packed column 20 is provided with heater 22 and temperature control unit 24. The outlet of the packed column 20 is connected to a gas measuring device 60, which includes an oxygen sensor or a carbon dioxide sensor and produces an electrical signal representing the concentration of $O_2$ or $CO_2$ in the gas flowing out of the packed column 20. In the case of detecting oxygen it is suitable to employ an oxygen sensor of the concentration cell type using stabilized zirconia. In the case of detecting carbon dioxide an IR gas analyzer can be used by way of example. The sample gas can be introduced into the packed column 20 by simply opening a valve (not shown) connected to the excimer laser 10 since the gas pressure in the excimer laser 10 is usually higher than the atmospheric pressure by more than 1 kg/cm². For determining the concentration of fluorine it suffices to keep the valve open for a few minutes. For correction of the output of the gas sensor 60, a calibration curve may be plotted in advance by analyzing known gas mixtures.

The output of the gas sensor 60, viz. an electrical signal $S_a$ representing the concentration of $O_2$ or $CO_2$ in the actually analyzed gas and, hence, the concentration of $F_2$ in the laser gas, is put into an indicator 62 and also to an arithmetic unit 64. For example, the arithmetic unit 64 utilizes a programmable controller to compute the amount of deviation of the fluorne concentration indicated by the input signal $S_a$ from the aimed concentration and produces a control signal $S_c$ indicating a proper amount of feed of fluorine into the excimer laser 10 for cancellation of the computed deviation. The control signal $S_c$ is transmitted to a gas feed device 66 which comprises a flow control device such as a mass flow controller having a valve of which the degree of opening is controllable, a flow rate detector and a flow rate adjusting device. By the gas feed device 66 fluorine gas can be supplied into the excimer laser 10 from a fluorine gas source 68 in a desired quantity or at a desired flow rate.

For cancelling the deviation of the detected fluorine concentration $P_d$ (%) in the laser gas from the aimed fluorine concentration $P_a$ (%), in the arithmetic unit 64 a proper flow rate R (cm³/min) of fluorine through the gas feed device 66 is computed, for example, by the following equation.

$$R(\text{cm}^3/\text{min}) = \frac{[P_a(\%) - P_d(\%)]}{100} \times V(\text{cm}^3) \times \frac{1}{M(\text{min})} \times K$$

where V is the gas volume in the excimer laser 10, M is the length of time in which the aimed fluorine concentration $P_a$ is to be reached and K is a correction factor.

It is possible to jointly use a control system of the above described type and a system for refining an excimer laser gas, for example, of the type shown in U.S. Pat. No. 4,740,982.

EXAMPLE 10

An excimer laser was operated with a laser gas consisting of 4.8 vol % of Kr, 0.2 vol % of $F_2$ and 95 vol % of He, and the control system of FIG. 5 was used to appropriately replenish the laser with fluorine gas.

A programmable controller in the arithmetic unit 64 was adjusted so as to maintain the predetermined concentration, 0.2 vol %, of $F_2$ in the laser gas by making computation using the above equation. A mass flow controller was used as the gas feed device 66.

The column 20 was a Monel metal column 8 mm in diameter and 100 mm in length, which was packed with 8 g of soda lime powder. The piping material was stainless steel (SUS 316), and both the column 20 and the piping were passivated by fluorine gas in advance. A zirconia oxygen sensor was used as the gas measuring device 60.

The excimer laser 10 was continuously operated so as to make laser oscillation at a predetermined rate, and an automatic valve (not shown) interposed between the laser 10 and the packed column 20 was opened for 2 min at intervals of 30 min to determine the concentration of $F_2$ in the laser gas and automatically supply an appropriate quantity of fluorine gas to the laser 10 by the action of the mass flow rate controller 66 so as to cancel the detected lowering of the concentration of fluorine.

While the operation of the excimer laser and the control system was continued for 5 hr, the output power of the laser remained very stable.

COMPARATIVE EXAMPLE 2

The operation of the excimer laser in Example 10 was repeated by using the same laser gas and under the same conditions. However, in this case the laser operation was continued without detecting the concentration of fluorine in the laser gas and without replenishing the laser gas with fluorine gas. The output power of the laser gradually lowered and in 4 hr became about 50% of the initial level.

What is claimed is:

1. A method of controlling the concentration of fluorine in an excimer laser gas during operation of an excimer laser to thereby stabilize the output power of the laser, the method comprising the steps of:

(a) passing a sample of the laser gas extracted from the excimer laser through a packed column comprising a compound which has no halogen atom and reacts with fluorine gas to form a solid fluoride and at least one of molecular oxygen and carbon dioxide, said solid fluoride being retained in said packed column;

(b) measuring the concentration of said at least one of molecular oxygen and carbon dioxide in a gas flowing out of said packed column and producing an electrical signal representing the measured concentration of said at least one of molecular oxygen and carbon dioxide as an indication of the concentration of fluorine in the laser gas;

(c) making a computing operation using said electrical signal to find a deviation of the concentration of fluorine in the laser gas from a predetermined concentration and producing a control signal representing an appropriate amount of supply of fluorine to the laser gas in the laser for cancellation of said deviation; and (d) regulating the supply of fluorine to the laser gas in the laser based on said control signal.

2. A system for controlling the concentration of fluorine in an excimer laser gas during operation of an excimer laser to thereby stabilize the output power of the laser, the system comprising:

a packed column comprising a compound which has no halogen atom and reacts with fluorine gas to form a solid halide and at least one of molecular oxygen and carbon dioxide, said solid halide being retained in said packed column;

means for passing a sample of the laser gas extracted from the excimer laser through said packed column;

a gas detecting means for measuring the concentration of said at least one of molecular oxygen and carbon dioxide in a gas flowing out of said packed column and producing an electrical signal representing the measured concentration of said at least one of molecular oxygen and carbon dioxide as an indication of the concentration of fluorine in the laser gas;

arithmetic means for making a computing operation using said electrical signal to find a deviation of the concentration of fluorine in the laser gas from a predetermined concentration and producing a control signal representing an appropriate amount of supply of fluorine to the laser gas in the laser for cancellation of said deviation; and flow rate control means for regulating the supply of fluorine to the laser gas in the laser based on said control signal.

3. A system according to claim 2, wherein said gas detecting means comprises an oxygen sensor of a concentration cell type using stabilized zirconia as an oxygen ion conductive solid electrolyte.

4. A system according to claim 2, wherein said gas detecting means comprises an infrared absorption spectrum analyzer.

5. An apparatus for analyzing a mixed gas containing fluorine gas but not oxygen and carbon dioxide gases to determine at least the concentration of the fluorine gas, the apparatus comprising:

a packed column comprising a compound which has no halogen atom and reacts with the fluorine gas to form a solid fluoride and at least one of molecular oxygen and carbon dioxide, said solid fluoride being retained in said packed column;

means for passing the fluorine containing mixed gas through said packed column;

a gas detecting means for measuring the concentration of said at least one of molecular oxygen and carbon dioxide in a gas flowing out of said packed column; and conversion means for converting the measured concentration of said at least one of molecular oxygen and carbon dioxide in the gas flowing out of said packed column to the concentration of fluorine gas in said mixed gas.

6. An apparatus according to claim 5, wherein said compound is selected from the group consisting of hydroxides, oxides, carbonates, hydrogen carbonates, sulfates and nitrates of alkali metals and alkaline earth metals and mixtures thereof.

7. An apparatus according to claim 5, wherein said compound is soda lime.

8. An apparatus according to claim 5, wherein said gas detecting means comprises an oxygen sensor of a concentration cell type using stabilized zirconia as an oxygen ion conductive solid electrolyte.

9. An apparatus according to claim 5, wherein said gas detecting means comprises a gas chromatography apparatus.

10. An apparatus according to claim 5, wherein said gas detecting means comprises an infrared absorption spectrum analyzer.

11. The apparatus according to claim 5, further comprising a heating means for keeping said packed column at a temperature above 100° C.

12. An apparatus for analyzing a mixed gas containing fluorine gas to determine at least the concentration of the fluorine gas, the apparatus comprising:

a first packed column comprising a compound which has no halogen atom and reacts with fluorine gas to form a solid first fluoride and at least one of molecular oxygen and carbon dioxide, said solid first fluoride being retained in said first packed column;

a packed column means which is substantially in parallel arrangement with said first packed column and comprises a material which reacts with fluorine gas to form a second solid fluoride without forming said at least one of molecular oxygen and carbon dioxide, said second solid fluoride being retained in said packed column means;

means for passing said mixed gas alternately and selectively through either of said first and second packed columns while blocking the other of said first and second packed columns;

a gas detecting means for alternately measuring the concentration of said at least one of molecular oxygen and carbon dioxide in a first gas flowing out of said first packed column and the concentration of said at least one of molecular oxygen and carbon dioxide in a second gas flowing out of said second packed column; and conversion means for subtracting the measured concentration of said at least one of molecular oxygen and carbon dioxide in said second gas from the measured concentration of said at least one of molecular oxygen and carbon dioxide in said first gas, thereby to determine a corrected concentration of said at least one of molecular oxygen and carbon dioxide formed in said first packed column and converting said corrected concentration to the concentration of fluorine gas in said mixed gas.

13. An apparatus according to claim 12, wherein said material is an element selected from the group consisting of Fe, Cr, Mn, Co, Zn, Ti, Zr, Sn and Pb.

14. An apparatus according to claim 12, wherein said packed column means comprises a second packed column containing an element selected from the group consisting of Si, Ge, P, Sb, S, Se, Te, W, Mo and V, and a third packed column which is disposed between said second packed column and said gas detecting means, said third packed column containing an alkali metal or alkaline earth metal compound that reacts with a gaseous fluoride flowing out of said second packed column to form said second solid fluoride.

15. The apparatus according to claim 14, further comprising heating means for keeping said third packed column at a temperature above 100° C.

16. The apparatus according to claim 12, wherein said compound is selected from the group consisting of hydroxides, oxides, carbonates, hydrogen carbonates, sulfates and nitrates of alkali metals and alkaline earth metals and mixtures thereof.

17. The apparatus according to claim 12, wherein said compound is soda lime.

18. The apparatus according to claim 12, wherein said gas detecting means comprises an oxygen sensor of a concentration cell type using stabilized zirconia as an oxygen ion conductive solid electrolyte.

19. The apparatus according to claim 12, wherein said gas detecting means comprises a gas chromatography apparatus.

20. The apparatus according to claim 12, wherein said gas detecting means comprises an infrared absorption spectrum analyzer.

21. The apparatus according to claim 12, further comprising heating means for keeping said first and second packed columns at a temperature above 100° C.

* * * * *

UNITED STATES PATENT AND TRADEMARK OFFICE
CERTIFICATE OF CORRECTION

PATENT NO. : 5,149,659

DATED : September 22, 1992

INVENTOR(S) : HAKUTA ET AL.

It is certified that error appears in the above-identified patent and that said Letters Patent is hereby corrected as shown below:

On the title page, Item [75] Inventors:
Please correct the spelling of the third inventor's name from "Takashi Suen. A." to --Takashi Suenaga--.

Signed and Sealed this

Seventh Day of December, 1993

Attest:

BRUCE LEHMAN

Attesting Officer     Commissioner of Patents and Trademarks